US008293801B2

(12) United States Patent
Ho

(10) Patent No.: US 8,293,801 B2
(45) Date of Patent: Oct. 23, 2012

(54) SKIN LIGHTENING METHOD

(76) Inventor: Thienna Ho, San Pablo, CA (US)

( * ) Notice: Subject to any disclaimer, the term of this patent is extended or adjusted under 35 U.S.C. 154(b) by 646 days.

(21) Appl. No.: 10/599,779

(22) PCT Filed: Apr. 8, 2005

(86) PCT No.: PCT/US2005/011915
§ 371 (c)(1),
(2), (4) Date: Jun. 28, 2007

(87) PCT Pub. No.: WO2005/099657
PCT Pub. Date: Oct. 27, 2005

(65) Prior Publication Data
US 2007/0264212 A1   Nov. 15, 2007

(51) Int. Cl.
*A61K 31/10* (2006.01)
(52) U.S. Cl. ........................................... 514/711
(58) Field of Classification Search ............ 424/401
See application file for complete search history.

(56) References Cited

U.S. PATENT DOCUMENTS

| | | | | |
|---|---|---|---|---|
| 4,296,130 | A * | 10/1981 | Herschler | 514/711 |
| 5,071,878 | A | 12/1991 | Herschler | |
| 6,183,758 | B1 | 2/2001 | Scott | |
| 6,328,987 | B1 | 12/2001 | Marini | |
| 6,444,234 | B1 * | 9/2002 | Kirby et al. | 424/725 |
| 6,497,860 | B1 | 12/2002 | Kawato | |
| 6,541,045 | B1 | 4/2003 | Charters et al. | |
| 6,573,299 | B1 * | 6/2003 | Petrus | 514/558 |
| 2002/0142019 | A1 | 10/2002 | Kuhnau | |

FOREIGN PATENT DOCUMENTS

WO   WO 9405279 A1 *   3/1994

OTHER PUBLICATIONS

Flick, Cosmetic and Toiletry Formulations, (1997), Noyes Publications, $2^{nd}$ edition, vol. 6, p. 146.*
Webster's ninth new collegiate dictionary, 1991, Merriam-Webster Inc., p. 269.*
Timmons, H., "Telling Inda's modern women they have power, even over their skin tone", New York Times, May 30, 2007, p. C5 (printed from ProQuest, on May 19, 2010).*
Pharmaceuticals Dosage Forms and Drug Delivery Systems, by H. Ansel (1950 5th Ed.), Lea & Feiger, pp. 310-320.

* cited by examiner

*Primary Examiner* — Gina C Justice
(74) *Attorney, Agent, or Firm* — Connolly Bove Lodge & Hutz LLP; Jonathan Jaech

(57) ABSTRACT

A skin lightening method for lightening the natural skin tone of a user, or for treating disorders of hyperpigmentation, includes delivering an effective amount of methyl sulfonyl methane (MSM) to an individual in need of skin lightening, until an noticeable lightening of skin tone is observed. Delivery may be accomplished by topical application, oral ingestion, or a combination of the foregoing. The skin lightening effect may be enhanced by application of an exfoliate during the treatment period. A transdermal patch may be used to deliver MSM to specific skin areas. A lightening of skin tone equivalent to one or two Fitzpatrick skin type classes may be achieved in about three to six months. After cessation of treatment, skin returns to its natural, genetically-determined tone.

11 Claims, 1 Drawing Sheet

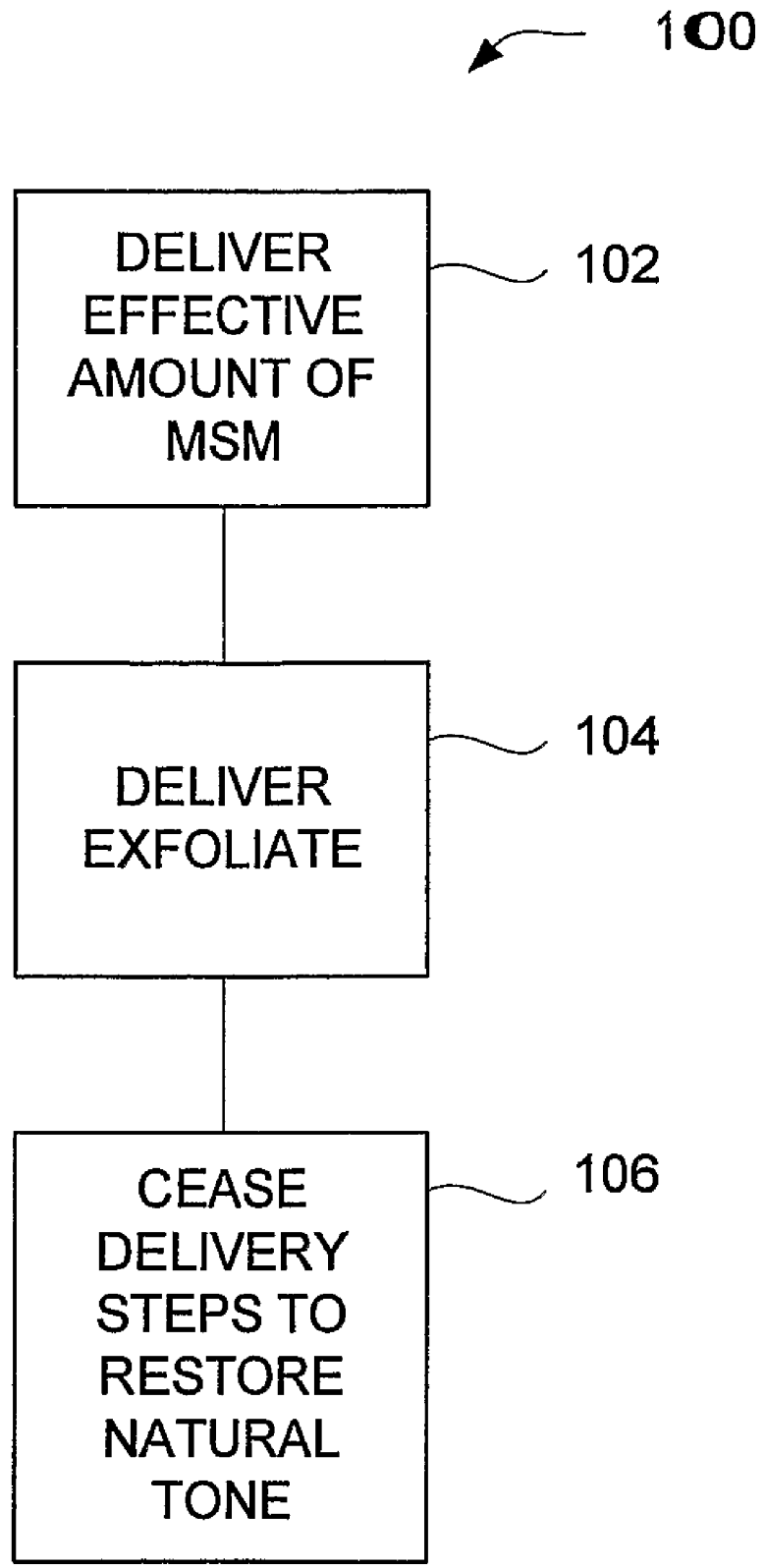

SKIN LIGHTENING METHOD

BACKGROUND OF THE INVENTION

1. Field of the Invention

The invention relates to a method for lightening the natural skin tone of a user, and more particularly to a method for lightening skin tone by delivery of a nutrient.

2. Description of the Related Art

Preparations for lightening skin tone are known in the art for lightening the overall natural skin color of individuals. Skin tone is sometimes characterized by the Fitzpatrick scale, which characterizes human skin tones in six classes, ranging from I (fair-skinned) to VI (black). Humans may sometimes desire to change their natural skin tone to a lighter shade as measured by the Fitzpatrick scale or other suitable measure, usually for cosmetic reasons. Skin lighteners are also useful for treating the excessively dark skin color caused by a dermatological condition known as hyperpigmentation, characterized by abnormally increased pigmentation.

A number of compounds are known to lighten skin tone when applied topically. The most popular of these is hydroquinone, which is generally effective in lightening skin tone and is available without a prescription. Notwithstanding its advantages, hydroquinone has been known to cause dermatological ochronosis, a progressive discoloration and degeneration of the skin, when used over an extended period of time. Alternative compounds for lightening skin color may also be available, some of which do not involve the delivery of hydroquinone. However, it is believed that known alternative methods have side effects or are not as effective as hydroquinone. Accordingly, there is a need for an effective method of lightening an individual's natural skin tone, that is non-toxic and without harmful side effects such as ochronosis.

SUMMARY OF THE INVENTION

The invention provides a method for skin lightening that is effective in lightening the natural skin tone of a user, and which is safe when topically applied to human skin. The method may also be used treat disorders of hyperpigmentation, and is believed to be safe when used for an extended period of time to maintain a lighter skin tone. When the method is discontinued, an individual's natural skin tone may gradually be restored without detriment to the individual's health or appearance.

In an embodiment of the invention, methy sulfonyl methane is delivered to an individual in an effective amount over an extended period of time, such as several months or longer, or until the desired degree of skin lightening is achieved. Methyl sulfonyl methane (MSM) is a naturally-occurring nutrient found in normal human diets. Plants are believed to concentrate MSM available in the soil and from the atmosphere, from where it becomes available in many foods. MSM represents an organic form of sulfur, in contrast to inorganic sulfites such as found in foodstuffs. Sulfur as provided by MSM and other compounds plays an important role in many body organs and systems. Although recognized by some as a beneficial nutrient and as a therapeutic substance for treatment of acne, arthritis, muscle pain, weak nails, dry or rough skin, and some other ailments, the use of MSM or skin lightening is not known in the art. Normal ingestion of MSM from dietary sources will not result in noticeable skin lightening. Known therapeutic uses are also believed to be ineffective in causing noticeable changes in skin tone.

Purified MSM is commercially available, and is usually derived from natural sources such as lignin, often as a breakdown product of dimethyl sulfoxide (DMSO). When purified, MSM is a pure, stable, white crystalline powder without unpleasant smell or taste. It may readily be compounded with various carriers in topical creams, gels, lotions, oils, or adhesives (such as used with trans-dermal patches). It may also be compounded with edible carriers for oral ingestion in pill or tablet form, or mixed with foods or beverages as a solid, or in solution or emulsion as a liquid.

In an embodiment of the invention, a topical preparation of a skin lightening composition containing MSM in an amount of approximately 1 to 25 weight percent, such as about 15%, or greater than 20% by weight, is applied to a person's skin in a daily regimen. In addition, an ingestible preparation of a skin lightening composition containing approximately 200 mg to 5000 mg MSM per serving, such as about 2000 mg twice daily, is ingested daily during the same period of time. Skin lightening equivalent to about one or two Fitzpatrick skin tone classes may be achieved in a few months time. When the regimen is ceased, skin reverts to its natural tone over a period of several months. In the alternative, an ingestible preparation of MSM may be taken until a desired amount of skin tone lightening is achieved, without topical application of MSM, or the MSM composition may be applied topically only, without ingestion of MSM. However, the combination of topical application and oral ingestion is believed to enhance both the degree of skin lightening, and the speed with which it may be achieved.

To further enhance skin lightening, the person's skin may be periodically treated with an exfoliate to stimulate skin cell renewal. For example, a water solution of lactic or gycolic acid may be applied periodically. Lactic acid solutions may be preferred for sensitive skin, in an embodiment of the invention, a 30% solution of lactic or glycolic acid may be applied twice weekly.

BRIEF DESCRIPTION OF THE DRAWINGS

FIG. 1 is a flow chart showing exemplary steps of a method according to the invention.

DETAILED DESCRIPTION OF THE PREFERRED EMBODIMENT

The present invention provides a method for skin lightening, that overcomes the limitations of prior art skin lightening methods. The method is believed safe and effective for lightening the natural skin color of a user, and also for reducing the symptoms of skin disorders characterized by abnormally increased pigmentation.

In humans and perhaps some other animals, melanin largely determines skin color, and is synthesized by the melanocytes in the basal layer of the epidermis. There are two melanin pigments, eumelanin and pheomelanin. Eumelanin is black and pheomelanin is yellow. The ratio of these two pigments in the skin determines how dark or light the skin will be. The synthesis of eumelanin and pheomelanin requires the amino acid tyrosine and the enzyme tyrosinase. Tyrosinase catalyzes the conversion of tyrosine into biochemical intermediates dopa and dopaquinone. Dopaquinone is the precursor of both eumelanin and pheomelanin in the process of melanogenesis, the biochemical processes which synthesize the melanins. Differences in the ratio of melanin pigments create wide variations in human skin color, ranging from "white" skin color to "black" skin color. Darker skinned individuals have a higher eumelanin to pheomelanin ratio.

While the invention is not limited thereby, it is believed that the delivery of an effective amount of MSM to the epidermal cells operates to lighten skin color by altering melanogenesis. In particular, MSM causes dopaquinone to be diverted towards the production of pheomelanin, rather than eumelanin, by safely and effectively increasing intracellular sulfur levels. When the intracellular sulfur concentration is relatively high, melanogenesis automatically leads to an increased synthesis of sulfhydryl-dopa conjugates, resulting in the synthesis of the lighter color pheomelanin instead of the darker colored eumelanin. The activity of MSM in skin lightening compositions is believed to result from its role in causing elevated intracellular sulfur levels, although the invention is not limited by this hypothesis. Therefore, the method according to the invention should be effective in lightening or altering the skin tone in any animal or human having a skin or body tone influenced or determined by intracellular sulfur concentration.

At the same time, methyl sulfonyl methane is a naturally occurring beneficial nutrient that is nontoxic, non-allergenic, and non-pyretic. It is believed to be both safe and effective when administered topically or when orally ingested, even over prolonged periods of time. Moreover, MSM has no undesirable pharmacological effects when taken in conjunction with other substances. Accordingly, the method may be used for cosmetic purposes by individuals desiring to achieve a lighter skin tone or to treat hyperpigmentation disorders. It is further anticipated that the method may be used safely and humanely to achieve a particular appearance in domestic livestock or pets, such as for animals having skin or fur color determined by a melanogenesis cycle like that of humans, or otherwise influenced or determined by intracellular sulfur concentration.

MSM may be delivered using various types of preparations to achieve lightening of skin tone. In particular, a skin lightening composition is provided in topical preparations which are applied directly to the skin, and also in orally ingestible preparations. Yet another alternative may be to deliver MSM in an adhesive composition using a transdermal patch. Topical preparations of the skin lightening composition may comprise MSM dissolved or mixed within a vehicle using any suitable method as known in the art. The vehicle may be a liquid solution, or it may be a cosmetic carrier such as a cream, a lotion, or a gel. Topical preparations of the skin lightening composition may contain MSM at an amount equal to approximately 1 to 25% weight percent MSM relative to the weight of the entire skin lightening composition. A higher weight percentage, such as at least about 15%, or between about 20-22%, is believed beneficial for more rapidly achieving lighter skin tone. Liquid solutions for topical application may include MSM in aqueous or non-aqueous solutions or emulsions. It is contemplated that a suitable skin lightening composition containing an effective amount of MSM may be combined with other cosmetics, such as moisturizers or perfumes, in order to provide a skin lightening composition with properties in addition to its skin lightening properties. By way of example, a skin lightening formula may comprise a moisturizing face and body cream into which the MSM has been blended. It is additionally contemplated that a skin lightening composition will be provided as a solid mixture, e.g., a mixture of MSM with vitamins and minerals that a user can mix with water and use for washing the face and body. Alternately, the skin whitening formula may be supplied as a liquid solution which may be directly used as a face and body wash.

MSM may also be compounded with known cosmetic compositions such as foundation, lipstick, or powder. For example, a relatively low concentration of MSM may be provided in a foundation for use as a daily maintenance of facial skin tone, that is, to maintain a lighter facial complexion after a desired amount of skin lightening has already been achieved using a higher concentration of MSM in a topical preparation as disclosed herein. While the invention is not limited to the use of low concentrations of MSM in cosmetic compositions, maintaining a relatively lower concentration (e.g., less than 10%) in such products may better maintain their desired cosmetic function.

Orally ingestible preparations of a suitable skin lightening composition containing MSM may be provided in liquid or in solid form. A single serving of an ingestible preparation may contain various suitable amounts of MSM, for example, approximately 200 mg to 5000 mg MSM per serving. Orally ingestible preparations of the skin whitening formula may be in an edible form such as a tablet, a pill, a capsule, or in powder form. MSM can also be compounded with a nutritional supplement that contains other vitamins, minerals, herbs, antioxidants, proteins, and/or amino acids for oral ingestion.

In accordance with the foregoing, therefore, a method 100 for causing the person to develop a skin tone noticeably lighter than the person's natural skin tone is disclosed herein, exemplary steps of which are shown in FIG. 1. At step 102, an effective amount of MSM is delivered to a person in need of a lighter skin tone. The person may desire a lighter tone for a cosmetic effect, or for treatment of a hyperpigmentation disorder. The delivery step may include any suitable combination of oral, topical, or transdermal application methods as known in the art.

A first procedure for performing step 102 is described in Table I below, at various dosage levels and application periods. The application periods indicated in the table were carried out in immediately successive periods on the same individual. Exemplary results are also shown in Table I, for an adult female test subject of approximately 45 kg weight having a skin type IV (moderate brown) according to the Fitzpatrick skin type classification. When the results indicate "no change" this indicates that no changes in skin tone were observed for the individual tested, and the amount of MSM delivered was therefore not an effective amount. Because of variation between individuals, the effective amount of MSM that should be delivered to cause a noticeable change in skin tone may vary somewhat. For example, dosage should be calculated based on body weight. Based on the disclosure herein, one of ordinary skill should be able to determine an effective dosage regimen without undue experimentation.

TABLE I

| Application Period | Oral MSM Supplement (mg) Taken Twice Daily (Morning and Evening) | Results |
|---|---|---|
| 3 months | 100 (200 mg daily) | No Change |
| 3 months | 250 (500 mg daily) | No Change |
| 3 months | 500 (1000 mg daily) | No Change |
| 3 months | 1000 (2000 mg daily) | Light Brown (skin type III) |

TABLE I-continued

| Application Period | Oral MSM Supplement (mg) Taken Twice Daily (Morning and Evening) | Results |
|---|---|---|
| 3 months | 2000 (4000 mg daily) | observed in constitutive skin such as under the arms, inner thighs, chests and nipples Olive (skin type II) observed in constitutive skin. Light Brown (skin type III) observed in facultative skin such as the neck, face, forearms, etc. Freckles on face also lightened |
| 3 months | 3000 (6000 mg daily) | Same results as 4000 mg per day |

Thus, Table I demonstrates that a noticeable overall body skin tone lightening of from 1 to 2 Fitzpatrick skin type classes may be achieved in an adult female having a natural Fitzpatrick skin type IV, by ingestion of 2000 to 6000 mg MSM daily, corresponding to about 45-135 mg/kg. For the tested individual, the optimal dose for maximum skin lightening appears to be between 2000 and 4000 mg (45 to 90 mg/kg) daily. For this individual, increasing the dosage to 6000 mg per day did not cause noticeable lightening relative to the 4000 mg regimen.

In an alternative embodiment, step 102 may be performed by oral delivery of MSM in combination with a topical application. Tale II below shows MSM delivery procedures that may be continued for 3-month periods to achieve skin lightening. Exemplary results are also shown in Table I, for the same test subject reported in Table I. Each row of the table indicates result for a procedure that was performed during one successive 3-month periods. For each procedure described in Table II, MSM delivered was in an effective amount for the reported test subject. Again, some variation in effective amount should be expected between individuals.

For the procedures described in Table II, a topical application may be prepared by dissolving the indicated amount of MSM in water to provide an approximately 15% by weight solution. For example, one tablespoon of MSM may be dissolved in 8 to 10 tablespoons of warm water to prepare the solution indicated in the first row. Then, the solution may be applied to the skin, which may be kept moistened with the solution for a period of approximately ten minutes or longer. The solution may be applied over the entire body, or only in areas where greater lightening of skin tone is desired. The indicated application may be performed once daily for approximately a three-month period. Shorter or longer application periods may also be effective, as may applications more than or less than once per day.

cation by solution may be continued for a period of about ten minutes daily, or longer. To more conveniently topically apply MSM to a specific area of skin, a transdermal patch may be used. A suitable patch may comprise a compatible carrier and adhesive material blended with any suitable percentage of MSM. When applied to the skin, the MSM will diffuse out of the adhesive patch into the adjacent skin tissue, thereby conveniently enabling delivery of MSM to a specific skin area for more prolonged periods of time. Suitable formulations for transdermal patches to deliver MSM should be readily ascertained by one of ordinary skill.

Referring again to FIG. 1, at step 104, a skin lightening effect may be enhanced by application of an exfoliant during the MSM treatment period. The exfoliant is believed to cause more darkly pigmented cells that formed during a pre-treatment period to be more raid shed. More lightly-pigmented cells formed during the treatment period may thus be more rapidly revealed, thereby more quickly achieving the desired change in skin tone. For example, the treatment regimen described in the second row of Table III may be combined with a twice-weekly rinse in an exfoliate solution. A suitable exfoliate solution may comprise, for example, a 30% solution of lactic or glycolic acid. A lactic acid solution may be more suitable for an individual with sensitive skin. In a test using an exfoliate in combination with oral and topical application, the test subject having a natural skin tone of Fitzpatrick type IV achieved and maintained a class III tone overall, with class II tone in constitutive skin areas.

Advantageously, the skin tone lightening that may be achieved by the method is not permanent. Thus, an individual may alter her skin tone for a temporary period to achieve a desired cosmetic effect for a temporary period, and then cease treatment. After cessation of treatment, skin should revert to its natural, genetically-determined tone within a period of about six months, depending on the degree of skin lightening

TABLE II

| Oral MSM Supplement (mg) Taken Twice Daily (Morning and Evening) | Topical Application of MSM in Water Solution to Face and Body | Results |
|---|---|---|
| 2000 (4000 mg daily) | 1 Tablespoon (10,000 mg) | Light olive (skin type III) observed in total body complexion |
| 2000 (4000 mg daily) | 2 Tablespoons (20,000 mg) | Constitutive skin much lighter than light olive; elsewhere light olive |
| 2000 (4000 mg daily) | 3 Tablespoons (30,000 mg) | Same as above |

Thus comparing Tables I and II, it is apparent that a greater skin lightening effect may be achieved by a combination of topical and oral delivery, than may be possible by oral delivery alone. In an embodiment of the invention, topical appliachieved by the original treatment. Cessation of treatment is indicated at step 106. Determination of the time to cease treatment may be determined by observing the skin of the person being treated. When the desired skin tone has been achieved, dosage levels may be reduced to maintain the skin tone. When it is no longer desired to maintain the lightened skin tone, treatment may be ceased altogether.

Having thus described a preferred embodiment of a method for lightening the natural skin tone of a person, it should be apparent to those skilled in the art that certain advantages of the within system have been achieved. It should also be appreciated that various modifications, adaptations, and alternative embodiments thereof may be made within the scope and spirit of the present invention. For example, specific delivery doses and modes have been illustrated, but it should be apparent that the inventive concepts described above would be equally applicable to doses and modes not set forth in the specific examples. The invention is defined by the following claims.

What is claimed:

1. A method for causing a person to develop a skin tone noticeably lighter than the person's natural skin tone, comprising delivering an effective amount of methyl sulfonyl methane to a person for developing a lighter skin tone by ingestion of the effective amount, at least until the person develops a skin tone noticeably lighter than before commencement of the delivery step, wherein the effective amount comprises orally administered doses in an amount of at least 133 mg of methyl sulfonyl methane per kilogram of body weight per day continuing for not less than three months.

2. The method of claim 1, further comprising delivering the effective amount of methyl sulfonyl methane by periodically ingesting in a compound comprising methyl sulfonyl methane and other ingredients.

3. The method of claim 2, further comprising delivering the effective amount of methyl sulfonyl methane by ingesting the compound further comprising at least one nutrient selected from vitamins, minerals, antioxidants, proteins, and amino acids.

4. The method of claim 1, further comprising delivering the effective amount of methyl sulfonyl methane also by periodic topical application of a compound comprising methyl sulfonyl methane.

5. The method of claim 1, further comprising delivering a portion of the effective amount of methyl sulfonyl methane in a compound comprising about 1 to 20 weight percent methyl sulfonyl methane for topical application.

6. The method of claim 1, further comprising delivering a portion of the effective amount of methyl sulfonyl methane in a compound comprising greater than about 20 weight percent methyl sulfonyl methane for topical application.

7. The method of claim 1, further comprising delivering a portion of the effective amount of methyl sulfonyl methane in a compound comprising about between about 20 to 22 weight percent methyl sulfonyl methane for topical application.

8. The method of claim 1, further comprising delivering an exfoliate to the person during the delivery of the methyl sulfonyl methane.

9. The method of claim 4, further comprising delivering an exfoliate to the person during the delivery of the methyl sulfonyl methane.

10. The method of claim 1, wherein the delivering the effective amount of methyl sulfonyl methane is performed at least about daily.

11. The method of claim 4, wherein the delivering the effective amount of methyl sulfonyl methane is performed at least about daily.

\* \* \* \* \*